United States Patent
Asami et al.

(10) Patent No.: US 6,989,351 B2
(45) Date of Patent: Jan. 24, 2006

(54) METABOLIC INHIBITORS AGAINST BRASSINOSTEROIDS

(75) Inventors: Tadao Asami, Tokyo (JP); Shigeo Yoshida, Tokyo (JP)

(73) Assignee: Riken, Saitama (JP)

( * ) Notice: Subject to any disclaimer, the term of this patent is extended or adjusted under 35 U.S.C. 154(b) by 0 days.

(21) Appl. No.: 10/332,994

(22) PCT Filed: Jul. 19, 2001

(86) PCT No.: PCT/JP01/06273

§ 371 (c)(1),
(2), (4) Date: Jun. 4, 2003

(87) PCT Pub. No.: WO02/07518

PCT Pub. Date: Jan. 31, 2002

(65) Prior Publication Data

US 2004/0259735 A1    Dec. 23, 2004

(30) Foreign Application Priority Data

Jul. 26, 2000    (JP) .............................. 2000-225486

(51) Int. Cl.
  *A01N 43/653*    (2006.01)
(52) U.S. Cl. ...................................... 504/272
(58) Field of Classification Search ............... 504/272, 504/293
See application file for complete search history.

(56) References Cited

U.S. PATENT DOCUMENTS 4,243,405 A    1/1981    Balasubramanyan et al. ...................... 504/181

(Continued)

FOREIGN PATENT DOCUMENTS

EP    0212841    3/1987

(Continued)

OTHER PUBLICATIONS

English Language Abstract of JP Appln. No. 56-34605, 1981.

(Continued)

*Primary Examiner*—S. Mark Clardy
(74) *Attorney, Agent, or Firm*—Greenblum & Bernstein, P.L.C.

(57) ABSTRACT

A brassinosteroid metabolism inhibitor, which comprises as an active ingredient a compound represented by the following formula (I) or (II):

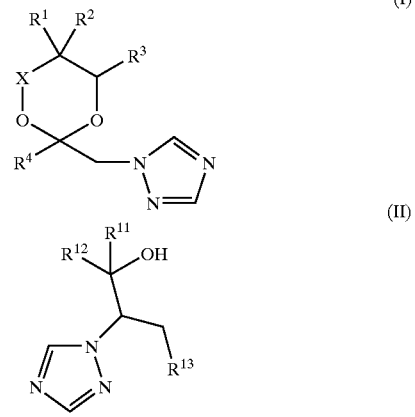

wherein $R^1$ and $R^2$ independently represent hydrogen atom or a lower alkyl group, $R^3$ represents a hydrogen atom, a lower alkyl group, or a lower alkoxyalkyl group, $R^4$ represents a phenyl group which may be substituted, X represents a single bond or —$CH_2$—, $R^{11}$ represents a lower alkyl group, a lower alkenyl group or a phenyl group which may be substituted, $R^{12}$ represents a lower alkyl group or a phenyl group which may be substituted, and $R^{13}$ represents a phenyl group which may be substituted, or a salt thereof.

16 Claims, 2 Drawing Sheets

U.S. PATENT DOCUMENTS

| | | | |
|---|---|---|---|
| 4,472,415 A | 9/1984 | Worthington et al. | 514/383 |
| 4,620,011 A | 10/1986 | Worthington et al. | 548/101 |
| 4,690,941 A | 9/1987 | Worthington et al. | 514/383 |
| 4,895,589 A | 1/1990 | Elliott et al. | 504/274 |
| 4,912,121 A | 3/1990 | Worthington et al. | 514/383 |
| 6,388,089 B1 | 5/2002 | Yoshida et al. | 548/262 |
| 6,495,572 B1 * | 12/2002 | Cohen | 514/339 |

FOREIGN PATENT DOCUMENTS

| | | |
|---|---|---|
| EP | 1270561 | 1/2003 |
| GB | 1529818 | 10/1978 |
| GB | 1544028 | 4/1979 |
| GB | 1595696 | 8/1981 |
| JP | 5634605 | 4/1981 |
| JP | 2000-53657 | 2/2000 |
| JP | 2001247413 | 9/2001 |
| JP | 2001247553 | 9/2001 |
| WO | 9844795 | 10/1998 |
| WO | 0009490 | 2/2000 |

OTHER PUBLICATIONS

English Language Abstract of JP Appln. No. 2000-53657, 2000.
English Language Abstract of JP Appln. No. 2001-247413.
Yokota, T., Trends in Plant Science, 2, pp. 137-143, 1997.
Mandava, N.B., Ann. Rev. Plant Physiol. Plant Mol. Biol., 39, pp. 23-52, 1988.
Schlagnhaufer, C., et al., Physiol. Plant., 61, pp. 555-558, 1984.
Iwasaki, T., et al., Plant Cell Physiol., 32(7), pp. 1007-1014, 1991.
Yamamoto, R., et al., Plant Cell Physiol., 38(8), pp. 980-983, 1997.
Azpiroz, R., et al., The Plant Cell, vol. 10, pp. 219-230, 1998.
Clouse, S.D., The Plant Journal, 10(1), pp. 1-8, 1996.
Fujioka, S., et al., Physiol. Plant., 100, pp. 710-715, 1997.
Feldman, K. A., et al., Science, 243, pp. 1351-1354, 1989.
Takahashi, T., et al., Genes & Dev., 9, pp. 97-107, 1995.
Kauschmann, A., et al., The Plant Journal., 9(5), pp. 701-713, 1996.
Szekeres M., et al., Cell, 85, pp. 171-182, 1996.
Li, J., et al., Science, 272, pp. 398-401, 1996.
Fujioka, S., et al., The Plant Cell, 9, pp. 1951-1962, 1997.
Nomura, T., et al., Plant Physiol., 113, pp. 31-37, 1997.
Yokota, T., et al., "Gibberillin", Springer Verlag, New York, pp. 339-349, 1991.
Neff, M. M., et al., Proc. Natl. Acad. Sci. USA, 96, pp. 15316-15323, 1999.
Min et al., Bioorg. and Med. Chem. Lett., 9:425-430, Feb. 8, 1999.
Asami et al., Plant Physiology, 123:93-99, May 2000.
Asami et al., Trends in Plant Science, 4(9):348-353, Sep. 1999.

* cited by examiner

METABOLIC INHIBITORS AGAINST BRASSINOSTEROIDS

TECHNICAL FIELD

The present invention relates to an inhibitor against brassinosteroid metabolism.

BACKGROUND ART

Brassinosteroids have been recently recognized as a new class of plant hormones through the combination of molecular genetics and researches on biosyntheses (Yokota, Trends in Plant Sci., 2, pp. 137–143, 1997). Since the chemistry of brassinosteroids was established, biological activities of these homologues have been extensively studied, and their notable actions on plant growth have been revealed, which include elongation of stalks, growth of pollen tubes, inclination of leaves, opening of leaves, suppression of roots, activation of proton pump (Mandava and Annu. Rev. Plant Physiol. Plant Mol. Biol., 39, pp. 23–52, 1988), acceleration of ethylene production (Schlagnhaufer et al., Physiol. Plant, 61, pp. 555–558, 1984), differentiation of vessel elements (Iwasaki et al., Plant Cell Physiol., 32, pp. 1007–1014, 1991; Yamamoto et al., Plant Cell Physiol., 38, pp. 980–983, 1997), and cell extension (Azpiroz et al., Plant Cell, 10, pp. 219–230, 1998).

Furthermore, mechanisms and regulations of physiological actions of brassinosteroids have been being revealed by variety of studies on their biosynthesis (Clouse, Plant J. 10, pp. 1–8, 1996; Fujioka et al., Physiol. Plant, 100, pp. 710–715, 1997). At present, 40 or more brassinosteroids have been identified. Most of C28-brassinosteroids are common vegetable sterols, and they are considered to be biosynthesized from campesterol, which has the same carbon side chain as that of brassinolide.

Several Arabidopsis mutants which show characteristic dwarfism have been isolated, i.e., dwfl: Feldman et al., Science, 243, pp. 1351–1354, 1989; dim: Takahashi et al., Genes Dev., 9, pp. 97–107, 1995; and cbb1: Kauschmann et al., Plant J., 9, pp. 701–703, 1996. Their structural photomorphogenesis and dwarfism (cpd: Szekeres et al., Cell, 85, pp. 171–182, 1997) and de-etiolation (det2: Li et al., Science, 272, pp. 398–401, 1996; Fujioka et al., Plant Cell, 9, pp. 1951–1962, 1997) are known. The mutants have deficiencies in the brassinosteroid biosynthetic pathway. Furthermore, a dwarf mutant of Pisum sativum was recently characterized, and the mutant was reported to be a brassinosteroid deficient mutant (Nomura et al., Plant Physiol., 113, pp. 31–37, 1997). In these plants, use of brassinolide is known to negate severe dwarfism of the mutants. Although these findings suggest that roles of brassinosteroids are indispensable for growth and development of plants, an effective tool other than the analysis of mutants has been desired to elucidate physiological importance of brassinolide.

As seen in researches of gibberellin action, specific inhibitors against the biosynthesis are generally very effective tools for elucidating physiological functions of endogenous substances. Specific inhibitors against brassinosteroid biosynthesis are expected to provide a new tool for understanding the functions of brassinosteroids. Uniconazole is a potent plant growth regulator (PGR) which inhibits oxidation employed by cytochrome P-450 in the steps of the gibberellin biosynthesis from ent-kaurene to ent-kaurenoic acid. Yokota et al. observed slight reduction of the amount of endogenous castasterone as a side effect of that compound (Yokota et al., "Gibberellin", Springer Verlag, New York, pp. 339–349, 1991). Although uniconazole in fact inhibits differentiation of vessel elements induced by brassinolide (Iwasaki et al., Plant Cell Physiol., 32, pp. 1007–1014, 1991), its inhibitory action against brassinolide is considered to be no more than an incidental action, because uniconazole essentially inhibits the gibberellin biosynthesis.

Several mutants deficient in biosynthetic enzymes are known for Arabidopsis, and their morphologic changes are unique to mutants with deficiency in the brassinosteroid biosynthesis. Therefore, the inventors of the present invention conducted intensive search for a compound inducing the morphologic changes unique to the mutants with the brassinosteroid biosynthesis deficiency to find a specific inhibitor against the brassinosteroid biosynthesis. As a result, they found that triazole compounds such as 4-(4-chlorophenyl)-2-phenyl-3-(1,2,4-triazoyl)butan-2-ol had the desired inhibitory action (Japanese Patent Unexamined Publication (Kokai) No. 2000-53657).

Meanwhile, it has been reported that genetic regulation of the brassinosteroid metabolism makes plants highly sensitive to brassinosteroids, and thus an effect of brassinosteroid administration is markedly enhanced (Neff, M. M., et al., Proc. Natl. Acad. Sci., USA, 96, pp. 15316–23, 1999). It may be possible to regulate plant growth by using this method. However, this technique has a problem that its application to an arbitrary plant at an arbitrary time is difficult. Further, it is known that plant growth can be regulated by administering brassinosteroids themselves to plants, and hence their yield and stress resistance can be enhanced. However, since brassinosteroids are expensive, their application as agricultural chemicals is difficult. It is expected that, if the brassinosteroid metabolism can be inhibited by a chemical agent, sensitivity of plants to brassinosteroids can be easily enhanced. However, no substance which inhibits the brassinosteroid metabolism has hitherto been known, and thus this method cannot be utilized.

DISCLOSURE OF THE INVENTION

An object of the present invention is to provide an inhibitor against the brassinosteroid metabolism. The inventors of the present invention conducted various studies to achieve the aforementioned object. As a result, they found that triazole compounds such as difenoconazole acted as a brassinosteroid metabolism inhibitor. The inventors further continued their researches, and found that the compounds represented by the following formula (I) or (II) inhibited the brassinosteroid metabolism, and these compounds had a regulatory action on plant growth by inhibiting the brassinosteroid metabolism. Thus, the present invention was achieved.

The present invention thus provides a brassinosteroid metabolism inhibitor which comprises, as an active ingredient, a compound represented by the following formula (I) or (II) or a salt thereof:

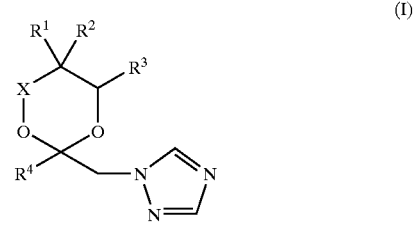

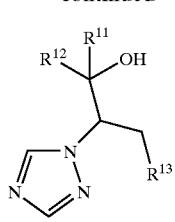

(II)

wherein R¹ and R² independently represent hydrogen atom or a lower alkyl group, R³ represents hydrogen atom, a lower alkyl group, or a lower alkoxyalkyl group, R⁴ represents a phenyl group which may be substituted, X represents a single bond or —CH₂—, R¹¹ represents a lower alkyl group, a lower alkenyl group, or a phenyl group which may be substituted, R¹² represents a lower alkyl group or a phenyl group which may be substituted, and R¹³ represents a phenyl group which may be substituted.

As preferred embodiments of the present invention, there are provided the aforementioned metabolism inhibitor, wherein R¹ and R² are hydrogen atoms, R³ is methyl group, R⁴ is 4-(4-chlorophenyl)oxy-2-chlorophenyl group or biphenyl-4-yl group, and X is a single bond; the aforementioned metabolism inhibitor, wherein R¹ and R² are hydrogen atoms, R³ is n-propyl group or methoxymethyl group, R⁴ is chlorophenyl group or methoxyphenyl group, and X is a single bond; and the aforementioned metabolism inhibitor, wherein R¹¹ is methyl group, R¹² is phenyl group, and R¹³ is 4-chlorophenyl group. As the brassinosteroid, brassinolide is preferred.

As another aspect of the present invention, there are provided a method for inhibiting brassinosteroid metabolism in a plant, which comprises the step of applying the compound represented by the aforementioned formula (I) or (II) or a salt thereof to a plant; and a method for regulating plant growth by inhibiting the brassinosteroid metabolism by using a metabolism inhibitor which comprises the compound represented by the aforementioned formula (I) or (II) or a salt thereof as an active ingredient.

According to a further aspect of the present invention, there is provided a plant growth regulator which comprises the aforementioned brassinosteroid metabolism inhibitor. This plant growth regulator has an inhibitory action against the brassinosteroid metabolism and can be used as a plant growth regulator for, for example, suppression of plant elongation, suppression of pollen growth, retention of freshness of flowers, use as an anti-stress agent for plants, weeds control, suppression of plant retrogradation, hypertrophism of roots and the like.

The present invention is also directed to a method for regulating plant growth by inhibiting brassinosteroid metabolism by applying to a plant a metabolism inhibitor which comprises a compound represented by the following formula (I) or a salt thereof

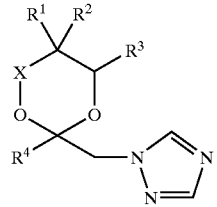

(I)

wherein R¹ and R² independently represent hydrogen atom or a lower alkyl group, R³ represents hydrogen atom, a lower alkyl group or a lower alkoxyalkyl group, R⁴ represents a phenyl group which may be substituted, X represents a single bond or —CH2—.

The present invention is also directed to a method for inhibiting brassinosteroid metabolism by applying to a plant a metabolism inhibitor which comprises a compound represented by the following formula (I) or a salt thereof

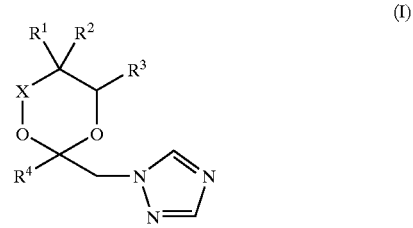

(I)

wherein R¹ and R² independently represent hydrogen atom or a lower alkyl group, R³ represents hydrogen atom, a lower alkyl group or a lower alkoxyalkyl group, R⁴ represents a phenyl group which may be substituted, X represents a single bond or —CH2—.

R¹ and R² can be hydrogen atoms, R³ can be methyl group, R⁴ can 4-(4-chlorophenyl)oxy-2-chlorophenyl group, and X can be a single bond.

R¹ and R² can be hydrogen atoms, R³ can be methyl group, R⁴ can be biphenyl-4-yl group, and X can be a single bond.

R¹ and R² can be hydrogen atoms, R³ can be n-propyl group or methoxymethyl group, R⁴ can be chlorophenyl group or methoxyphenyl group, and X can be a single bond.

The brassinosteroid can be brassinolide.

BEST MODE FOR CARRYING OUT THE INVENTION

Figure 1:
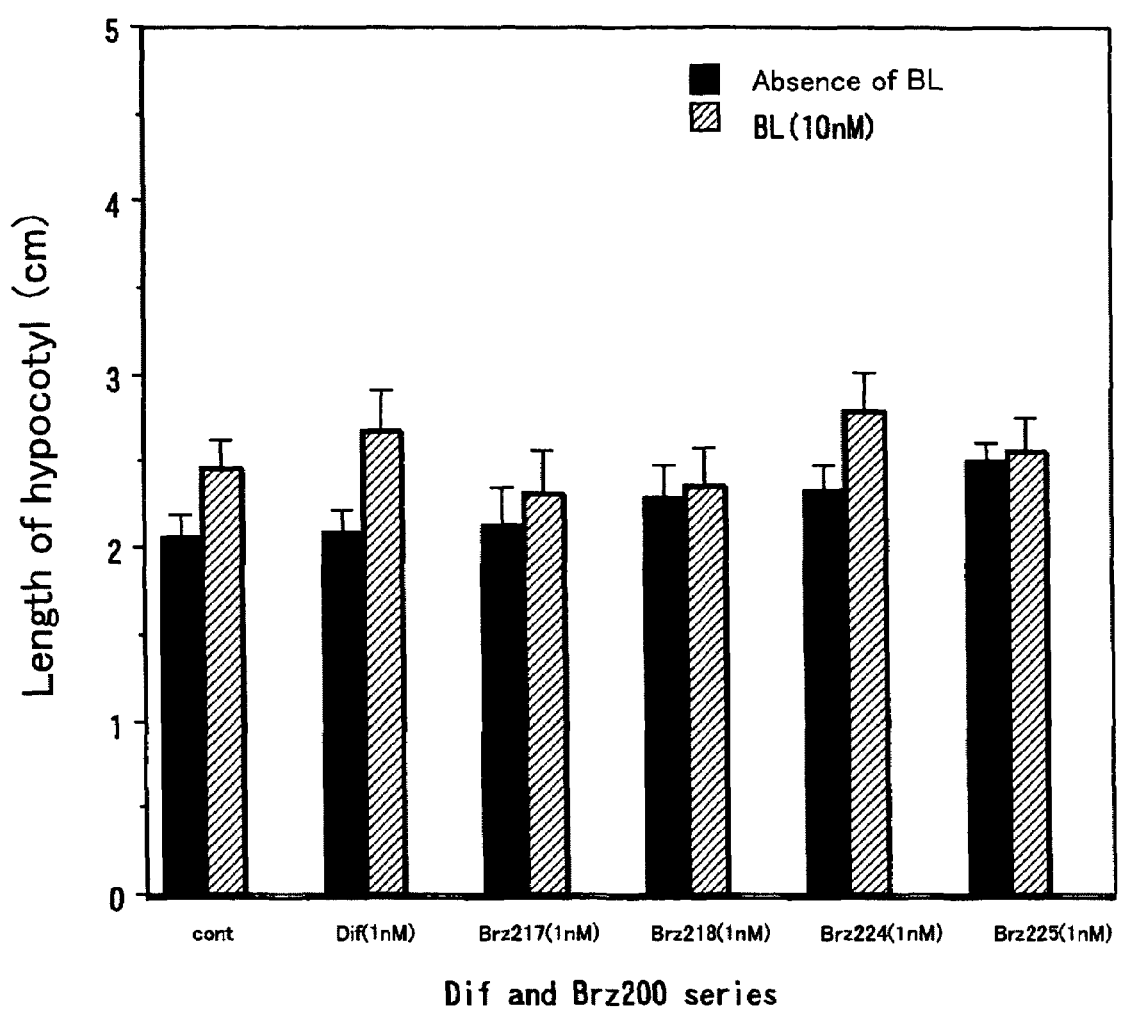
FIG. 1 shows the result of elongation of cress hypocotyl by the metabolism inhibitor of the present invention on day 5 after seeding.

The entire disclosures of the specification of Japanese Patent Application No. 2000-225486 (filed on Jul. 26, 2000) are incorporated in the disclosures of the present specification by reference.

In the aforementioned formula (I), as the lower alkyl group represented by R¹, R² or R³, a linear or branched alkyl group having 1 to about 6 carbon atoms can be used (the same shall apply to a lower alkyl moiety of an alkoxy group or the like having the alkyl moiety). Examples thereof include methyl group, ethyl group, n-propyl group, isopropyl group, n-butyl group, sec-butyl group, tert-butyl group and the like. It is preferred that both R¹ and R² are hydrogen atoms. Further, it is also preferred that R¹ and R² are hydrogen atoms, and R³ is a linear lower alkyl group (for example, methyl group, ethyl group, n-propyl group, n-butyl group and the like). It is particularly preferred that R¹ and R² are hydrogen atoms, and R³ is methyl group. Examples of the lower alkoxyalkyl group represented by $R^3$ include, for example, methoxymethyl group and the like. X is preferably a single bond.

When the phenyl group represented by $R^4$ is substituted, types, numbers and substituting positions of substituents are not particularly limited. For example, the phenyl group may have preferably 1 to 3, more preferably 1 or 2 of substituents. Where the phenyl group has two or more substituents, they may be the same or different.

Examples of the substituent on the phenyl group include, for example, a halogen atom (any of fluorine atom, chlorine atom, bromine atom and iodine atom), a lower alkyl group (methyl group, ethyl group and the like), a lower cycloalkyl group (cyclopropyl group and the like), a halogenated lower alkyl group (trifluoromethyl group and the like), a lower alkoxy group (methoxy group, ethoxy group and the like), amino group, a mono- or dialkylamino group, carboxyl group, an alkoxycarbonyl group (ethoxycarbonyl group and the like), an alkanoyl group (acetyl group and the like), an aroyl group (benzoyl group and the like), an aralkyl group (benzyl group and the like), an aryl group (phenyl group and the like), an aryloxy group (phenoxy group and the like), a heteroaryl group (pyridyl group and the like), a heteroaryloxy group (pyridyloxy group and the like), a heterocyclic group (pyrrolidinyl group and the like), hydroxyl group, nitro group, cyano group and the like. However, the substituents are not limited to these examples.

As the substituent on the phenyl group, a lower alkyl group, a halogen atom, a halogenated lower alkyl group, a lower alkoxy group, a halogenated lower alkoxy group, hydroxyl group, an aryl group, and an aryloxy group are preferred. A halogen atom, a phenyl group (it may further have one or more substituents on the ring), a phenoxy group (it may further have one or more substituents on the ring) and a halogenated lower alkyl group are more preferred. More preferred as the substituent on the phenyl group represented by $R^4$ are one or more substituents selected from the group consisting of a halogen atom, a substituted or unsubstituted phenyl group, and a substituted or unsubstituted phenoxy group, and particularly preferred is a substituent selected from the group consisting of chlorine atom, phenyl group and 4-chlorophenoxy group.

More specifically, examples of the substituted phenyl group represented by $R^4$ include 2-chlorophenyl group, 4-chlorophenyl group, 3,4-dichlorophenyl group, 2,4-dichlorophenyl group, 3,4-difluorophenyl group, 2,4-difluorophenyl group, 4-bromophenyl group, 4-trifluoromethoxyphenyl group, 4-toluyl group, 4-trifluoromethylphenyl group, 3-trifluoromethylphenyl group, 4-hydroxyphenyl group, 4-methoxyphenyl group, 2-chloro-4-trifluoromethylphenyl group, 3-chloro-4-trifluoromethylphenyl group, 4-bromo-2-chlorophenyl group, biphenyl-4-yl group, (4-chlorophenyl)oxy-2-chlorophenyl group and the like. Among them, biphenyl-4-yl group and 4-(4-chlorophenyl)oxy-2-chlorophenyl group are preferred.

In the aforementioned formula (II), $R^{11}$ represents a lower alkyl group, a lower alkenyl group or a phenyl group which may be substituted. As the lower alkyl group, a linear or branched alkyl group having 1 to about 6 carbon atoms can be used. Examples include methyl group, ethyl group, n-propyl group, isopropyl group, n-butyl group, sec-butyl group, tert-butyl group, isobutyl group and the like. Among them, methyl group and ethyl group are preferred, and methyl group is particularly preferred. As the lower alkenyl group, a linear or branched alkenyl group having 2 to about 6 carbon atoms can be used. Examples include vinyl group, allyl group, 2-butenyl group and the like.

When the phenyl group represented by $R^{11}$ is substituted, types, numbers and substituting positions of substituents are not particularly limited. For example, the phenyl group may have preferably 1 to 3, more preferably 1 or 2 of substituents. Where the phenyl group has 2 or more substituents, they may be the same or different. As the substituent on the phenyl group, for example, any of those mentioned above can be used.

As the lower alkyl group or the phenyl group which may be substituted represented by $R^{12}$ and the phenyl group which may be substituted represented by $R^{13}$, groups similar to each of those mentioned for the groups represented by $R^{11}$ can be used. $R^{12}$ is preferably an unsubstituted phenyl group, and 2,4-difluorophenyl group and the like may be used as a substituted phenyl group. Examples of the substituted phenyl group represented by $R^{13}$ include 4-chlorophenyl group and the like.

The compounds represented by the aforementioned formula (I) or (II) may have one or more asymmetric carbon atoms. Optically active compounds and diastereoisomers in pure forms based on the asymmetric carbon atoms as well as any mixtures of the isomers (for example, mixtures of two or more kinds of diastereoisomers), racemates and the like can be used as an active ingredient of the metabolism inhibitor of the present invention. Furthermore, the compounds represented by the aforementioned formula (I) or (II) can form acid addition salts, and may further form acid addition salts depending on the type of the substituent. The types of the salts are not particularly limited, and examples of the salts include salts with mineral acids such as hydrochloric acid, and sulfuric acid, salts with organic acids such as p-toluenesulfonic acid, methanesulfonic acid, and tartaric acid, metal salts such as sodium salts, potassium salts, and calcium salts, ammonium salts, salts with organic amines such as triethylamine, salts with amino acids such as glycine, and the like.

Specific examples of the compounds represented by the formula (I) include those described in the specification of Japanese Patent Application No. 2000-057564 as well as difenoconazole shown below, Brz401 and the like. Specific examples of the compounds represented by the formula (II) include the following brassinazole as well as the compounds described in the specifications of Japanese Patent Unexamined Publication No. 2000-53657 and Japanese Patent Application No. 2000-57565.

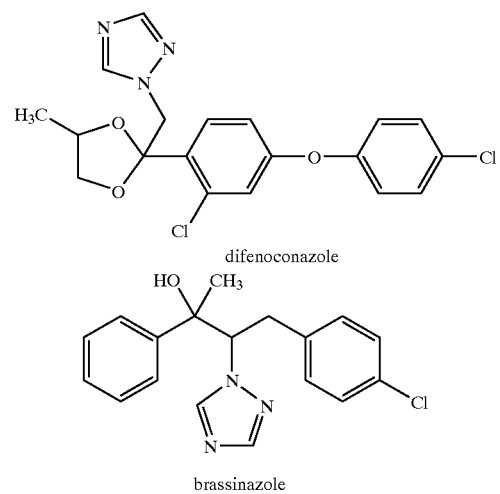

difenoconazole brassinazole

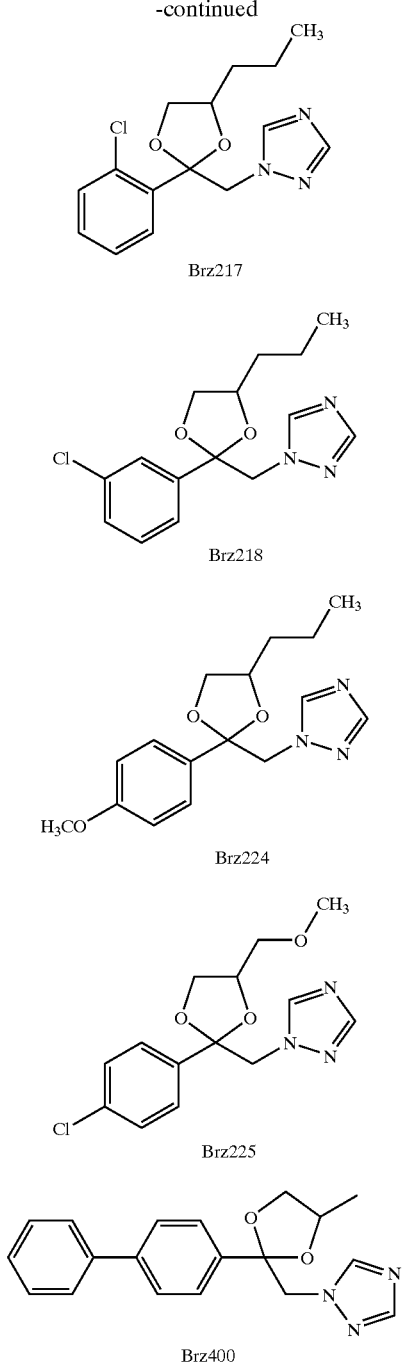

Brz217

Brz218

Brz224

Brz225

Brz400

The compounds represented by the formula (I) can be prepared by the methods described in literature (for example, Zeitschrift fur Naturforschung, 44c, pp. 85–96, 1989 and the like), or they are available as commercial products. For example, a compound represented by the formula (I) wherein $R^1$ and $R^2$ are hydrogen atoms, $R^3$ is n-propyl group, $R^4$ is 2,4-dichlorophenyl group, and X is a single bond is available from Ciba-Geigy as a fungicide (propiconazole). Furthermore, novel compounds can be prepared according to the methods described in literature. The compounds represented by the formula (II) can be easily prepared according to the methods described in Japanese Patent Unexamined Publication No. 2000-53657 and the specification of Japanese Patent Application No. 2000-57565.

The compounds represented by the formula (I) or (II) or salts thereof, as an active ingredient of the metabolism inhibitor of the present invention, have inhibitory action against the metabolism of brassinosteroids which are plant hormones. When the metabolism inhibitor of the present invention is applied to a plant, the inhibitor can exert the same effect as that obtained when a brassinosteroid is administered to a plant, and plant growth regulation based on the inhibition against the brassinosteroid metabolism can be achieved. The term "plant growth regulation" used in the specification should be construed in its broadest sense including, for example, regulation of plant elongation such as dwarfing of plants, pollen growth regulation, retention of flower freshness, use as a plant anti-stress agent (against heat, dryness, coldness or the like), weed control by regulation of reproduction, suppression of plant retrogradation, control of hypertrophy of root and the like. Furthermore, brassinosteroids encompass compounds such as brassinolide, and the metabolism inhibitor of the present invention can inhibit the metabolism of any compound encompassed in brassinosteroids.

The metabolism inhibitor of the present invention can be formulated, for example, as an agricultural composition by using formulation additives well known in the art. Forms of the agricultural composition are not particularly limited, and any forms that can be used in the art may be chosen. For example, compositions in the forms of emulsions, liquids, oils, water soluble powders, wettable powders, flowables, powders, subtilized granules, granules, aerosols, fumigants, pastes and the like can be used. The methods for manufacturing the agricultural composition are also not particularly limited, and any methods available to those skilled in the art can be appropriately employed. As the active ingredient of the metabolism inhibitor of the present invention, two or more of the compounds represented by the aforementioned formula (I) or (II), or salts thereof, may be used in combination. Further, other active ingredients of agricultural chemicals such as insecticides, fungicides, insecticidal and fungicidal agents, herbicides and the like may be incorporated.

Methods of application and doses of the metabolism inhibitor of the present invention can be suitably chosen by those skilled in the art depending on conditions including a purpose of application, a dosage form, a plot to be treated and the like. The metabolism inhibitor of the present invention may sometimes inhibit brassinosteroid biosynthesis when used at a high concentration, and may exhibit an action on plants opposite to the action of the metabolism inhibitor. Such a phenomenon is recognized in difenoconazole, Brz217, Brz218, Brz224, Brz225 and the like, which are typical examples of the metabolism inhibitor of the present invention. Therefore, the metabolism inhibitor of the present invention is preferably applied to plants at a relatively low concentration. However, concentrations to achieve optimum action can be appropriately determined by those skilled in the art by referring to the following examples.

EXAMPLES

The present invention will be explained more specifically with reference to examples. However, the scope of the present invention is not limited to the following examples.

Example 1

Experimental Method For Growing Plants (Using Agar Medium)

This method was a common method for measurement of activity of each of the compounds. The activity as a metabolism inhibitor was measured as an activity for accelerating elongation of cress hypocotyl. Seeds were sterilized by immersion in 1% hypochlorous acid for 20 minutes and washed 5 times with sterilized water. Then, the seeds were sown on a 1% agar medium containing 0.5×MS medium and 1.5% sucrose, and grown in Agripot (purchased from Kirin Brewery Co. Ltd.) under sterilized conditions. A test compound was prepared beforehand so as to be a predetermined concentration on this agar medium, and a control plot not added with the compound was prepared for each of the tests. The plants were grown at 25° C. under a cycle of 16-hour light and 8-hour dark conditions. After a predetermined growth period, activity determination was conducted by measuring the length of the cress lower hypocotyl.

Figure 2:
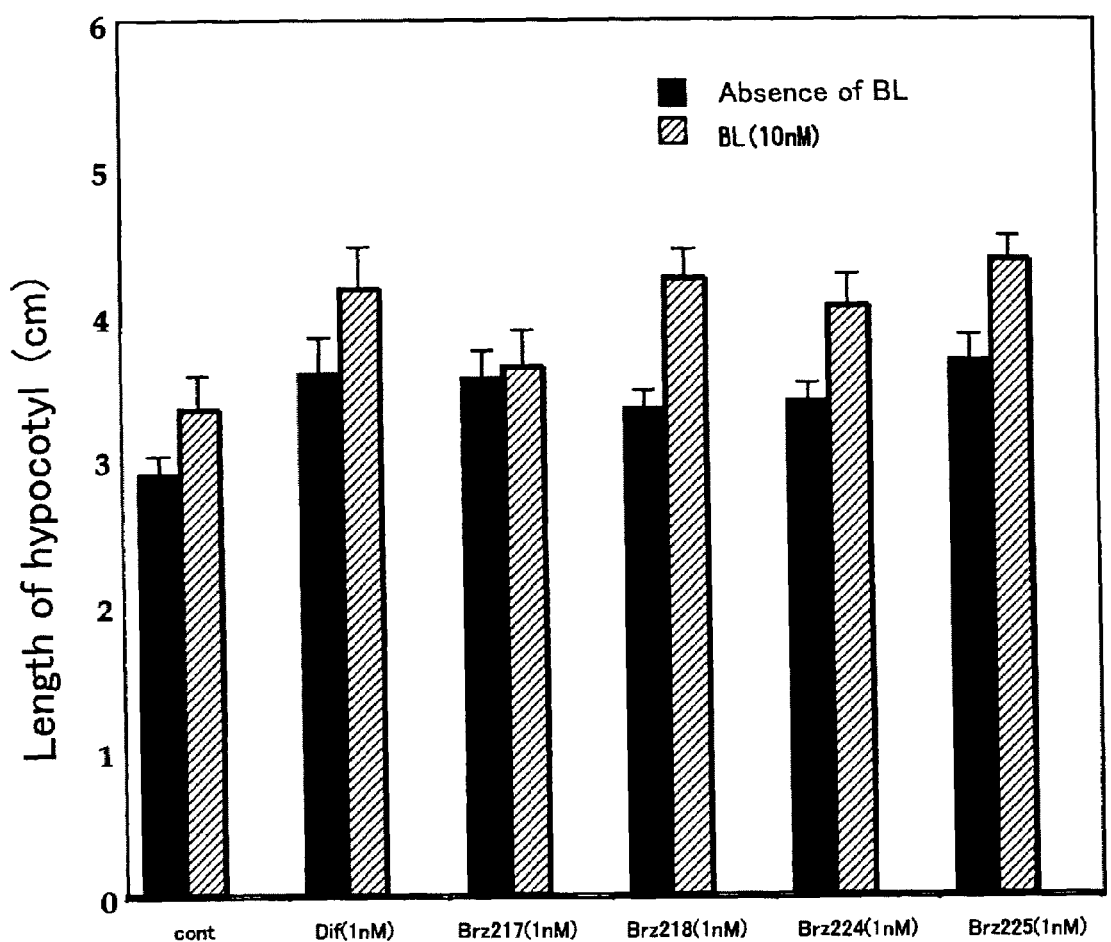
FIG. 2 shows the result of elongation of cress hypocotyl by the metabolism inhibitor of the present invention on day 14 after seeding.

As shown in FIGS. 1 and 2, when each compound was applied, acceleration of elongation of the cress hypocotyl was observed compared with the control (in the figures, Dif represents difenoconazole, and the compounds such as Brz217 are as described above). Further, when brassinolide was applied in combination, an acceleration tendency of the elongation was observed.

Example 2

To examine whether the accelerating activity on elongation of the cress hypocotyl was on the basis of the inhibitory activity against the metabolism of brassinolide, which is considered to be a practically active brassinosteroid, activity of the compounds was examined in degradation system associated with oxidation of the 26th position of brassinolide. Immature seeds of Pisum sativum were used as plant materials. Brassinolide was added to a cell free system, and metabolic activity was determined by quantifying the compound at the right end in the following scheme to examine inhibitory action of difenoconazole against metabolism.

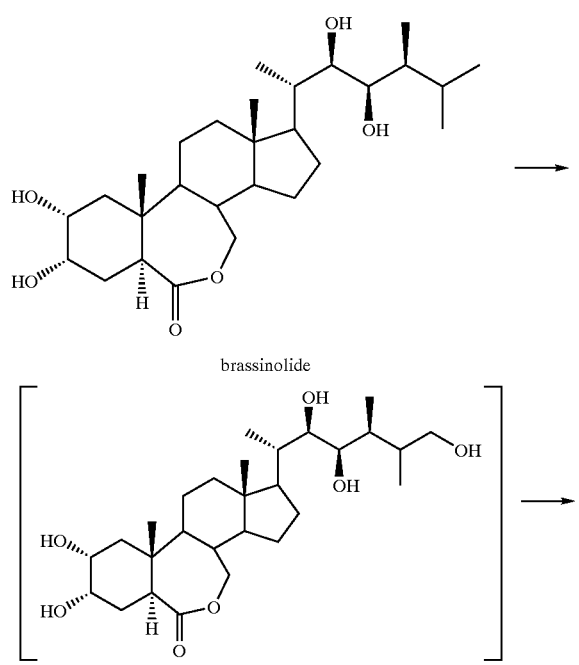

brassinolide

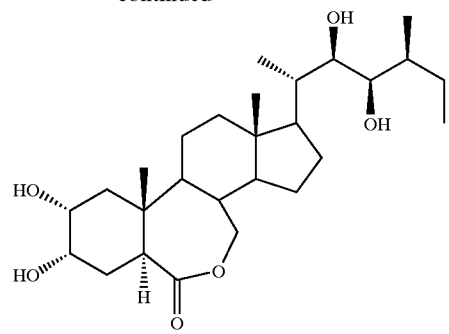

TABLE 1

| Compound | Concentration | Ratio of metabolism inhibition degree (%) relative to control |
|---|---|---|
| Control | | 0 |
| Difenoconazole | 0.01 μM | 0 |
| Difenoconazole | 0.1 μM | 7 |
| Difenoconazole | 1.0 μM | 72 |
| Difenoconazole | 10 μM | 76 |

It was revealed that difenoconazole inhibited the metabolic process of brassinolide by 72% at a concentration of 1 μM. Although the results are different from the test results in Example 1 in terms of effective concentration, the difference is considered to be attributable to the difference of plant species.

INDUSTRIAL APPLICABILITY

The compounds represented by the formula (I) or (II) or salts thereof, which are active ingredients of the metabolism inhibitors of the present invention, have inhibitory action against the brassinosteroid metabolism, and can be used as plant growth regulators, for example, for suppression of plant elongation, suppression of pollen growth, retention of freshness of flowers, use as anti-stress agents for plants, weeds control, suppression of plant retrogradation, hypertrophism of roots and the like.

What is claimed is:

1. A method for regulating plant growth by inhibiting brassinosteroid metabolism by applying to a plant a metabolism inhibitor in a concentration effective for plant growth regulation which comprises a compound represented by the following formula (I) or a salt thereof (I)

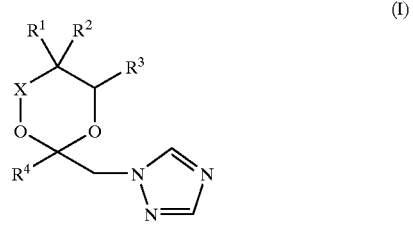

wherein $R^1$ and $R^2$ independently represent hydrogen atom or a lower alkyl group, $R^3$ represents hydrogen atom, a lower alkyl group or a lower alkoxyalkyl group, $R^4$ represents a phenyl group which may be substituted, X represents a single bond or —CH2—.

2. The method according to claim 1, wherein $R^1$ and $R^2$ are hydrogen atoms, $R^3$ is methyl group, $R^4$ is 4-(4-chlorophenyl)oxy-2-chlorophenyl group, and X is a single bond.

3. The method according to claim 1, wherein $R^1$ and $R^2$ are hydrogen atoms, $R^3$ is methyl group, $R^4$ is biphenyl-4-yl group, and X is a single bond.

4. The method according to claim 1, wherein $R^1$ and $R^2$ are hydrogen atoms, $R^3$ is n-propyl group or methoxymethyl group, $R^4$ is chlorophenyl group or methoxyphenyl group, and X is a single bond.

5. The method according to claim 1, wherein the brassinosteroid is brassinolide.

6. The method according to claim 2, wherein the brassinosteroid is brassinolide.

7. The method according to claim 3, wherein the brassinosteroid is brassinolide.

8. The method according to claim 4, wherein the brassinosteroid is brassinolide.

9. A method for inhibiting brassinosteroid metabolism by applying to a plant a metabolism inhibitor in a concentration effective for plant growth regulation which comprises a compound represented by the following formula (I) or a salt thereof.

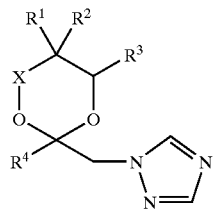

(I)

wherein $R^1$ and $R^2$ independently represent hydrogen atom or a lower alkyl group, $R^3$ represents hydrogen atom, a lower alkyl group or a lower alkoxyalkyl group, $R^4$ represents a phenyl group which may be substituted, X represents a single bond or —CH2—.

10. The method according to claim 9, wherein $R^1$ and $R^2$ are hydrogen atoms, $R^3$ is methyl group, $R^4$ is 4-(4-chlorophenyl)oxy-2-chlorophenyl group, and X is a single bond.

11. The method according to claim 9, wherein $R^1$ and $R^2$ are hydrogen atoms, $R^3$ is methyl group, $R^4$ is biphenyl-4-yl group, and X is a single bond.

12. The method according to claim 9, wherein $R^1$ and $R^2$ are hydrogen atoms, $R^3$ is n-propyl group or methoxymethyl group, $R^4$ is chlorophenyl group or methoxyphenyl group, and X is a single bond.

13. The method according to claim 9, wherein the brassinosteroid is brassinolide.

14. The method according to claim 10, wherein the brassinosteroid is brassinolide.

15. The method according to claim 11, wherein the brassinosteroid is brassinolide.

16. The method according to claim 12, wherein the brassinosteroid is brassinolide.

* * * * *